(12) United States Patent
Firestone et al.

(10) Patent No.: US 8,168,746 B2
(45) Date of Patent: May 1, 2012

(54) BIOMIMETIC MATERIALS FOR PROTEIN STORAGE AND TRANSPORT

(75) Inventors: Millicent A. Firestone, Elmhurst, IL (US); Philip D. Laible, Villa Park, IL (US)

(73) Assignee: UChicago Argonne, LLC, Chicago, IL (US)

( * ) Notice: Subject to any disclaimer, the term of this patent is extended or adjusted under 35 U.S.C. 154(b) by 987 days.

(21) Appl. No.: 12/148,518

(22) Filed: Apr. 18, 2008

(65) Prior Publication Data
US 2008/0319169 A1    Dec. 25, 2008

Related U.S. Application Data

(60) Provisional application No. 60/925,306, filed on Apr. 18, 2007.

(51) Int. Cl.
*C07K 14/00* (2006.01)
(52) U.S. Cl. .......................................... 530/300; 514/2
(58) Field of Classification Search .................. None
See application file for complete search history.

(56) References Cited

U.S. PATENT DOCUMENTS 6,537,575 B1    3/2003    Firestone et al.

OTHER PUBLICATIONS

Aveldano, Marta, "Phospholipid solubilization during detergent extraction of Rhodopsin from photoreceptor disk membranes", Archives of Biochemistry and Biophysics, 324(2): 331-343 (1995).*
C. Kirmaier, et al., Journal of Physical Chem. B, 106, 1799 (2002).
D. D. Lasic, et al., Chem Rev. 95, 2601 (1995).
C. R. Safinya, Curr Opin Struct Biol 11, 440 (Aug. 2001).
A. T. Brunger, et al., Acta Crystallographica D54, 905 (1998).
M. Firestone, et al., Journal of Physical Chem. B, 104, 11 (Mar. 23, 2000), 2433.
P.D. Laible, et al., Electron-Transfer Dynamics of Photosynthetic Reaction Centers in Thermoresponsive Soft Materials, J. Physical Chem. B., 109, 23679-23686 (2005).
M. A. Firestone, et al., Magnetic Field-Induced Ordering of a Polymer-Grafted Biomembrane-Memetic Hydrogel, J. Phys Chem B 104, No. 11, pp. 2434-2438 (Mar. 23, 2000).

* cited by examiner

*Primary Examiner* — Anand Desai
(74) *Attorney, Agent, or Firm* — Cherskov Flaynik & Gurda, LLC

(57) ABSTRACT

The invention provides a method for the insertion of protein in storage vehicles and the recovery of the proteins from the vehicles, the method comprising supplying isolated protein; mixing the isolated protein with a fluid so as to form a mixture, the fluid comprising saturated phospholipids, lipopolymers, and a surfactant; cycling the mixture between a first temperature and a second temperature; maintaining the mixture as a solid for an indefinite period of time; diluting the mixture in detergent buffer so as to disrupt the composition of the mixture, and diluting to disrupt the fluid in its low viscosity state for removal of the guest molecules by, for example, dialysis, filtering or chromatography dialyzing/filtering the emulsified solid.

19 Claims, 14 Drawing Sheets

SQUARES = SAMPLES IN INVENTED FLUID

CIRCLES = SAMPLES IN BUFFER

SOLID LINES = SAMPLES STORED AT 4 DEGREES C

DASHED LINES = SAMPLES STORED AT 20 DEGREES C

DOTTED LINES = SAMPLES STORED AT 32 DEGREES C

Figure 8A

| Entry | Common Name | Structure (Full Name) | C | CMC (mM) |
|---|---|---|---|---|
| 1 | Trialkylamine-N-oxides | 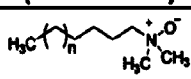 Alkyl-N,N-dimethylamine-N-oxide (n = 1, 5, 6, 7) | Z | 22 (n=5) <br> 1.4 (n=7) |
| 2 | LAPAO | 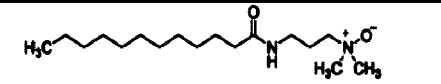 3-Laurylamido-N,N'-dimethylpropylamine oxide | Z | 3.3 |
| 3 | Octyl-2-hydroxyethyl sulfoxide | 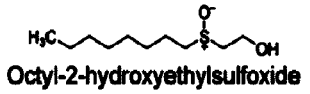 Octyl-2-hydroxyethylsulfoxide | Z | 15.8 |
| 4 | Fos-Choline-8 | 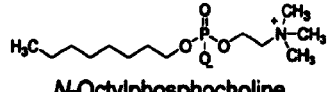 N-Octylphosphocholine | Z | 114 |
| 5 | Zwittergent 3-12 | 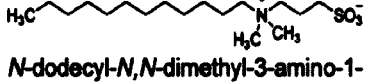 N-dodecyl-N,N-dimethyl-3-amino-1-propanesulfonate | Z | 2.7 |
| 6 | DHPC | 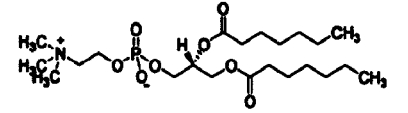 1,2-Diheptanoyl-sn-Glycero-3-Phosphocholine | Z | 1.4 |

| Entry | Common Name | Structure (Full Name) | C | CMC (mM) |
|---|---|---|---|---|
| 7 | DOPC |  1,2-Dioleoyl-sn-Glycero-3-Phosphocholine | Z | n.d. |
| 8 | CHAPS |  3-[(3-Cholamidopropyl) dimethylammonio]-1-propanesulfonate | Z | 8 |
| 9 | CTAB |  Cetyltrimethylammonium bromide | C | 1.0 |
| 10 | HPC |  Hexadecylpyridinium chloride | C | 16 |
| 11 | SDS |  Sodium Dodecylsulfate | A | 8.2 |
| 12 | Deriphat 160C |  Monosodium N-Lauryl-beta-Iminodipropionic Acid | A | 0.026 |

| Entry | Common Name | Structure (Full Name) | C | CMC (mM) |
|---|---|---|---|---|
| 13 | Deriphat 151C (n = 1 to 15) |  Cocaminopropionic acid | A | 0.01 |
| 14 | Sodium Cholate |  3α,7α,12α-Trihydroxy-5β-cholan-24-oic acid | A | 4 |
| 15 | N,N-Dimethylundecyl amine |  N,N-Dimethylundecylamine | N | n.d. |
| 16 | MEGA-10 |  Decanoyl-N-methyl glucamide | N | 6 |
| 17 | HEGA-10 |  Decanoyl-N-hydroxyethyl glucamide | N | 7 |
| 18 | HECAMEG |  Methyl-6-O-(N-heptylcarbamoyl)-α-D-glucopyranoside | N | 19.5 |

Figure 8D

| Entry | Common Name | Structure (Full Name) | C | CMC (mM) |
|---|---|---|---|---|
| 19 | Glucopyranosides | Alkyl-β-D-glucopyranoside (n = 1,2) | N | 19 (n=1) 6.5 (n=2) |
| 20 | Thiogluco pyranosides | Heptyl-β-D-thioglucopyranoside | N | 29 |
| 21 | Alkyl-β-D-maltoside | Alkyl-β-D-maltopyranoside (n = 1,3,4,5,6) | N | 19.5 (n=1) 1.8 (n=3) 0.59 (n=4) 0.17 (n=5) 0.03 (n=6) |
| 22 | CYMAL-3 | Cyclohexylpropyl-β-D-maltoside | N | 38 |
| 23 | $C_8E_4$ (m = 1, n = 1) $C_{10}E_5$ (m = 3, n = 2) $C_{12}E_8$ (m = 5, n = 5) $C_{12}E_9$ (m = 5, n = 6) | Alkylalkoxyethylene | N | $C_8E_4$ = 7 $C_{10}E_5$ = 0.8 $C_{12}E_8$ = 0.1 $C_{12}E_9$ = 0.08 |
| 24 | Triton X-100 | Polyethylene glycol tert-octylphenyl ether | N | 0.23 |

BIOMIMETIC MATERIALS FOR PROTEIN STORAGE AND TRANSPORT

PRIORITY

This utility application claims the benefit of U.S. Provisional Application No. 60/925,306, filed on Apr. 18, 2007.

CONTRACTUAL ORIGIN OF INVENTION

The United States Government has rights in this invention pursuant to Contract No. W-31-109-ENG-38 between the U.S. Department of Energy and the University of Chicago, representing Argonne National Laboratory.

BACKGROUND OF THE INVENTION

1. Field of the Invention

This invention relates to a method for receiving and storing biological molecules, and more specifically, this invention relates to a method for storing proteins in their native state for assay or application and/or delivery to sites remote from the initial extraction and storage facilities.

2. Background of the Invention

Membrane proteins represent an extremely important class of biomolecules whose functions are vital to human health. As such, they comprise the vast majority of drug targets being pursued at present. In contrast to soluble proteins, much less is known about membrane proteins, primarily due to the difficulty of producing sizeable quantities of them in natively-folded, functional, and relatively pure form.

In order for membrane proteins to subsist in the aqueous environments required for most chromatographies and analyses, they must first be removed from their native lipid bilayer, usually through the use of detergents, and remain soluble in detergent environments for further characterization or subsequent crystallization attempts. Membrane protein-detergent complexes, upon purification, are most frequently preserved either through flash freezing, the use of non-native, synthetic architectures, or by reconstitution of samples into liposomes.

Flash freezing is often employed in attempts to extend the viability and structure of some biomolecules. Indeed, it is well established that the function of most membrane proteins is short-lived, sometimes just hours, when removed from their native environs. Although flash freezing works successfully for some protein and detergent combinations, it is hardly a universal tool for extending the viability of proteins in their native states or maintaining the native structure of the proteins. Generally, cycling across the liquid-solid transition (i.e., the action of freezing and thawing) has deleterious effects on the integrity of samples and excludes the use of this approach, irrespective of the length of storage in the frozen state.

Non-native, synthetic architectures have been explored as possible biomolecule preservation systems. The "maintenance" and sequestration of membrane proteins in non-native, synthetic architectures that mimic native membranes have involved the use of various model systems that can be grouped into three general types: monolayer, planar bilayer, or mesophases. However, each of these systems have their drawbacks.

The study of monolayers at an air-water interface via the use of a Langmuir trough is well suited for measurement of surface activity, but it models only the outer leaflet of the bilayer and, thus, does not provide an appropriate model for the study of molecular species that fully insert into a lipid bilayer. Similarly, although supported lipid bilayers provide a more accurate model of natural biomembranes, they suffer from a serious limitation in that the underlying substrate (typically, glass) can interact detrimentally with molecules that fully insert into the bilayer (e.g., not providing a suitable water layer).

Bicelles (oblate bilayer micelles) offer an improvement over simple micelles since their architecture better models a native biomembrane. Wide-scale implementation of bicelles is limited, however, since stable field alignment can be induced only over a narrow, often elevated temperature range. In addition, undesirable bicelle surface-protein associations can lead to phase separation and poor temporal stability. A. T. Brunger et al. *Acta Crystallographica* D54, 905 (1998).

Phospholipid bilayer discs serving as model membranes also have been utilized to store proteins. These nanodiscs consist of a membrane scaffold protein and a detergent solubilized phospholipid, and self-assemble upon addition of the desired protein and removal of the detergent used in the isolation and purification of the membrane protein target. The protein-stabilized assemblies, however, tend to be heterogeneous, complicate certain spectroscopic measurements, and inhibit interactions among protein partners that are frequently required for proper function.

Liposomes are aqueous compartments enclosed by lipid membranes. Liposomes represent a better alternative to freezing in many cases. Micelles and liposomes have been successfully employed in fundamental physicochemical studies (liposomes have primarily been used in functional assays with considerably less in the area of structure) and have found some practical application in the area of drug delivery and DNA transfection. D. D. Lasic, D. Needham, Chem. Rev. 95, 2601 (1995). C. R. Safinya, *Curr Opin Struct Biol* 11, 440 (August, 2001). However, because they do not possess long-range translational order (diffraction peaks) and cannot be ordered asymmetrically, they are not candidate materials from which detailed structural information of guest membrane proteins can be obtained. Membrane proteins reconstituted into liposomes are not amenable to many assays commonly employed to probe structure and function. Furthermore, to remove membrane proteins from liposomes, one must re-isolate protein components by reintroducing a high concentration of detergent into the sample.

A need exists for a method to preserve proteins in their native state to make further characterization of their structures and functions possible. The method should facilitate indefinite storage of the protein and, where possible, allow in situ characterization of the native protein to assess its structural integrity and functional state.

A need also exists for a biocompatible medium capable of providing a cellular mimetic environment for the encapsulation and organization of a wide range of proteins (including soluble and membrane) and complexes. Ideally, such a medium should possess the ability to be highly ordered. In this way, it could be adapted to low-to-medium resolution structural studies of the organized proteins using a range of techniques, including NMR and EPR spectroscopies, small-angle X-ray or neutron scattering/diffraction, and optical spectroscopy.

SUMMARY OF INVENTION

An object of the present invention is to provide a method for isolating and maintaining protein in its native state that overcomes many of the disadvantages of the prior art.

Another object of the invention is to provide a method for extracting protein from its native environment and store that extracted protein indefinitely. A feature of the invention is the use of a fluid comprised of phospholipid, a polymer and a co-surfactant. An advantage of the utilization of this fluid is that it provides an environment preventing the protein from hydrating (i.e., to be suspended in an unnatural configuration in an aqueous environment), thereby increasing its stability one-thousand fold over previous archiving methods. Storage half lives of greater than nine months have been realized. In an embodiment of the invention, a storage half life of at least 260 days was achieved, wherein after this duration of time protein remained in a useable state in one of the complex fluid-containing environments.

Still another object of the present invention is to provide a vehicle to extract, store, transport, and reuse membrane proteins. A feature of the invention is that the stability of purified membrane proteins is markedly improved by their incorporation into polymer/lipid-based complex fluids, most notably at elevated temperatures. An advantage of the invention is that the tunability of this fluid allows for (i) ease of incorporation of the guest molecules, (ii) use of these proteo-complex fluid samples in a wide range of spectroscopies, and (iii) ease of recovery of guest molecules that can be utilized in subsequent structural characterization studies.

The invention provides a method for the insertion of protein in storage vehicles and the recovery of the proteins from the vehicles, the method comprising supplying isolated protein; mixing the isolated protein with a fluid, the fluid comprising phospholipids, non-ionic polymers, and a surfactant, so as to form a mixture; cycling the mixture between a first temperature and a second temperature; maintaining the mixture as a solid for an indefinite period of time; diluting the mixture in detergent buffer so as to disrupt the composition and later recovering the isolated protein by dialysis, filtration, centrifugation, electrophoresis, or chromatography.

In an embodiment of the invention, saturated (i.e., tightly packed) phospholipids were utilized, along with lipopolymers.

BRIEF DESCRIPTION OF DRAWING

The invention together with the above and other objects and advantages will be best understood from the following detailed description of the preferred embodiment of the invention shown in the accompanying drawing, wherein:

FIGS. 8A-D are tables of exemplary detergents used within the system.

DETAILED DESCRIPTION OF THE INVENTION

Figure 1:
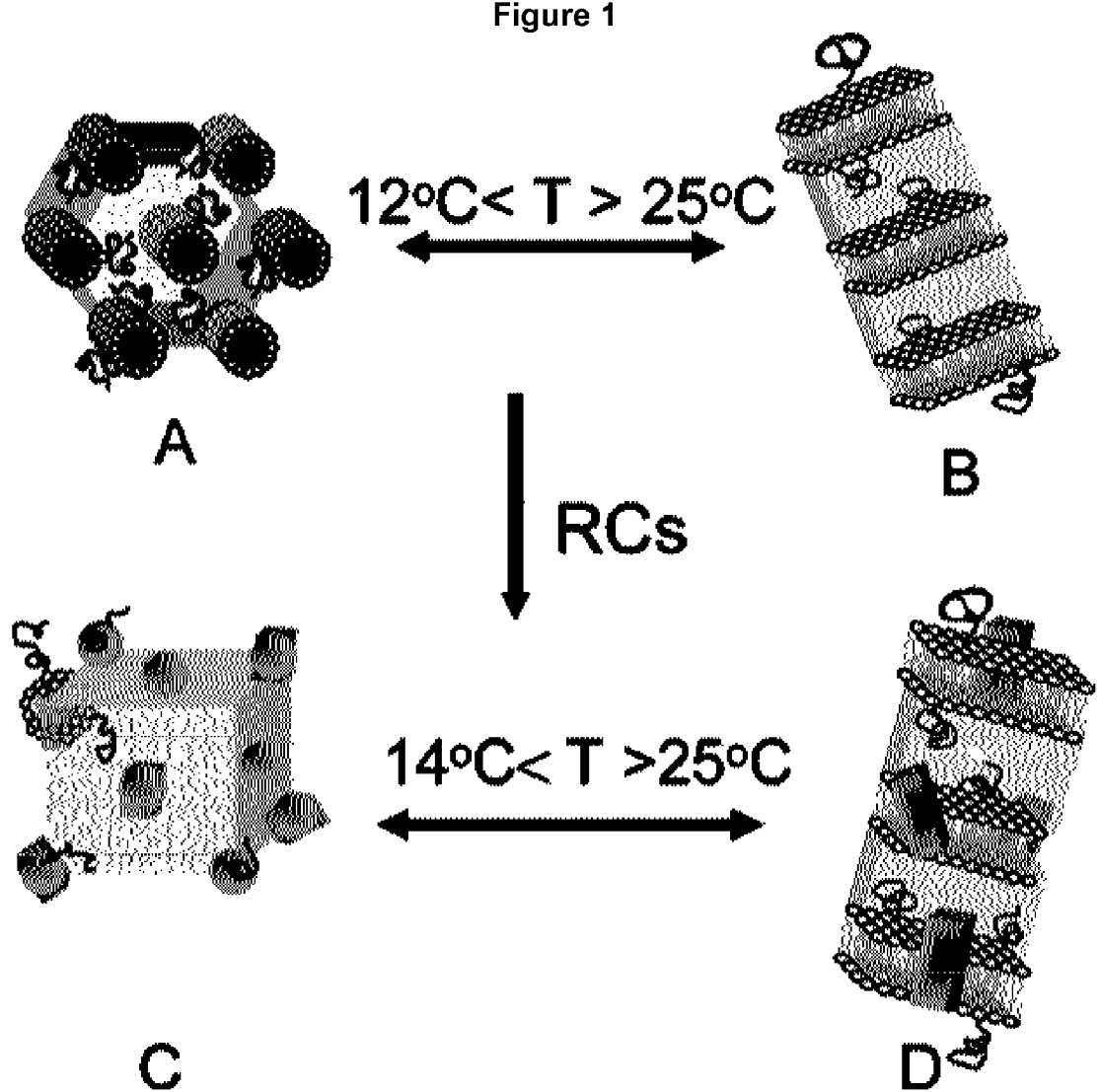
FIGS. 1A-D are schematic representations of the topology of polymer-grafted lipid-based complex fluid showing the effects of various temperatures and the presence of guest protein molecules; (A) In the cold, normal hexagonal phase; (B) above the phase transition, expanded lamellar structure; (C) doped with reaction centers (RCs) below the phase transition, proposed cubic micellar phase; (D) doped with RCs above the phase transition, expanded lamellar structure.
Figure 2:
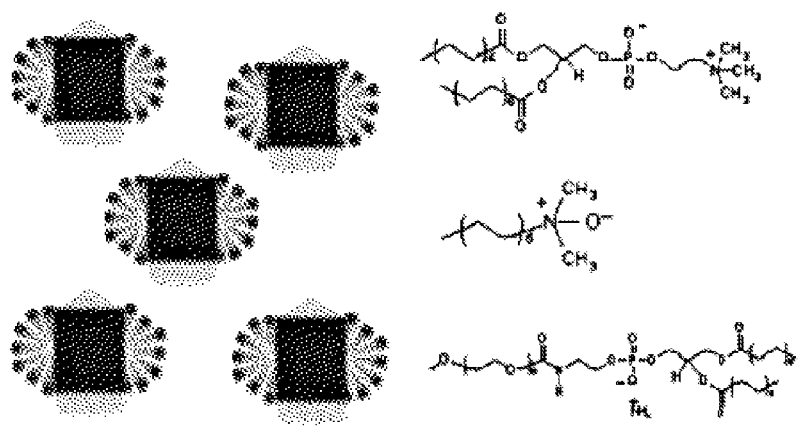
FIG. 2 is a schematic for a protocol for the formation of proteocomplex fluids and the recovery of membrane proteins, soluble proteins, protein complexes stored therein, in accordance with features of the present invention.
Figure 2:
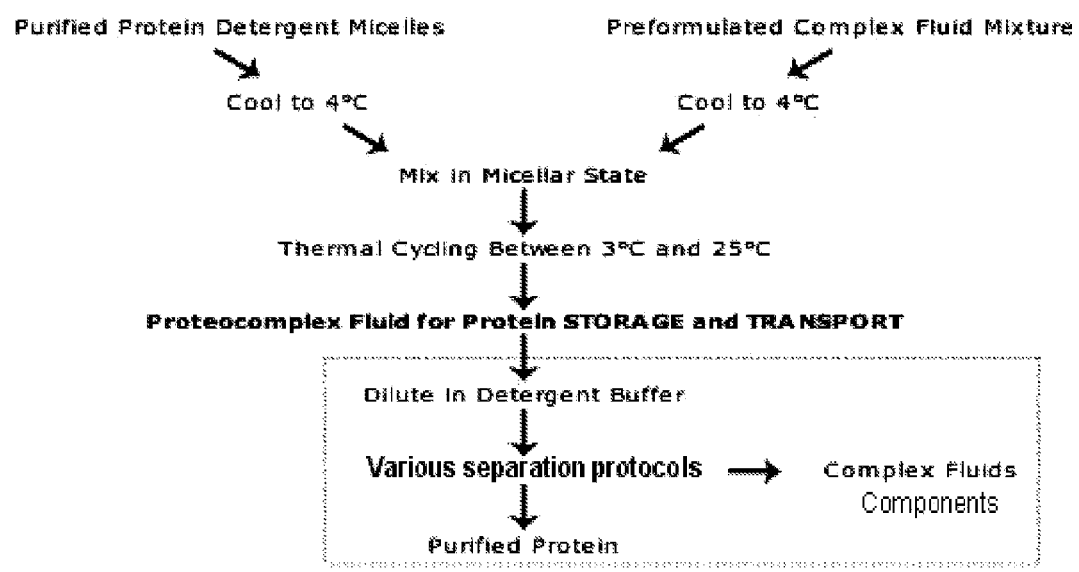

The inventors have developed a method for storing proteins in their native state. The method facilitates the storage and transport of a myriad of types of proteins for later application, sale, characterization, and analysis. Membrane proteins, soluble proteins, and complexes of such proteins (whereby the complexes are of membrane proteins, soluble proteins, or a combination thereof) are all envisioned as extraction, storage and transport candidates.

The invented protocol enables viable protein to be sequestered indefinitely in within lipids (i.e., penetrating a portion or all of the bilayer), outside lipids (i.e., within the interlamellar spacing) or a combination of within the lipids and outside the lipids.

The resulting protein/liquid vehicle construct is capable of sequestering a myriad of biomolecules, including, but not limited to DNA, RNA, metabolite, cofactor, or other molecules ranging from a few atoms to several hundred amino acids or several thousand basepairs.

Amphiphiles (surfactants, phospholipids, polymers, etc.) self-associate in water to form aggregates (mesophases) featuring monolayer or bilayer structures. These noncovalent aggregates, often referred to in general terms as "complex fluids", can provide an ordered, native-like (i.e., physiological pH and ionic strength, high water concentration, and a lipid membrane environment) matrix in which to selectively partition a variety of biological molecules.

The use of complex fluids to store protein offer several advantages over the prior art and have proven to be a stabilizing environment for isolated proteins, protein complexes, and other types of complexes such as protein-ligand, protein-DNA, protein-RNA, RNA-DNA, protein-cofactor, etc.

The inventors have developed a polymer-grafted lipid-based complex fluid consisting of a quanternary mixture of water, a phospholipid (dimyristoylphosphatidylcholine), a lipopolymer comprising poly(ethylene) oxide terminally grafted on to a headgroup of dimyristoylphosphatidylethanolamine, and a zwiterrionic surfactant (N,N-dimethyldodecylamine N-oxide). In an embodiment of the invention, a polymer/lipid-based complex fluid was utilized to sequester membrane proteins in their native states. The complex fluid comprises a saturated phospholipid (1,2-Dimyristoyl-sn-Glycero-3-Phosphocholine, DMPC), a polymer (1,2-Dimyristoyl-sn-Glycero-3-Phosphoethanolamine-N-[Methoxy(Polyethylene glycol)-2000], DMPE), and a co-surfactant (N,N-dimethyldodecylamine-N-oxide, LDAO). When combined in water, these components self-assemble, and the resulting material possess an inverted phase transition, existing in a liquid-crystalline gel phase at temperatures above~20° C. and in a low viscosity (i.e. liquid and not solid), micellar state at reduced temperatures.

The physicochemical and structural properties of this material are tunable, achieved through variations in nonionic polymers (one example being polyethylene glycol chains) and water content. Water can be present from 60-90 percent, while a preferred embodiment has polymer present at less than 20 mole percent. The gel phase mimics a biological membrane and could be used to stabilize reconstituted integral membrane proteins for long-term storage or for transport between site of purification and site of application, use and/or characterization.

The liquid state at lower temperatures serves as the phase in which membrane proteins can be introduced to the materials. Once the protein is loaded into the complex fluid, separation and/or ordering of the sequestered proteins is effected via electrophoresis or isoelectric fusing. Details of magnetic field-induced ordering of biomembranes, applicable in ordering the instant protein/fluid liquor, are found in Firestone, et al. *Jnl Phys Chem B* 104,No. 11, pp 2434-2438, the entirety of which is incorporated herein by reference.

Once formed this complex fluid is optically transparent, allowing for the conduction of membrane protein structural assays, mainly those based upon spectroscopy. Proteins can be extracted readily from the complex fluid by dilution into a detergent buffer when in the low viscosity state, followed by separation protocols, e.g., dialysis at 4° C., chromatography, filtration centrifugation or electrophoresis. Viscosity states range from solid to liquid. Dilution occurs in a buffer which includes the detergent initially used in making the complex fluid.

Here, for illustrative purposes only, we evaluate the use of these complex fluids as a stabilizing agent for photosynthetic reaction centers (RCs), alluding to its use in storing and transporting membrane protein samples. As such, the invention should not be construed as relegated solely to the sequestration and preservation of native RC protein. Similarly, several detergents are suitable for the myriad of lipid mixtures envisioned by the inventors, such detergents including nonionic, charged (anionic, cationic), zwitterionic, designer detergents, and amphiphilic molecules. FIGS. 8A-D provide exemplary detergents within these classes.

Figure 3:
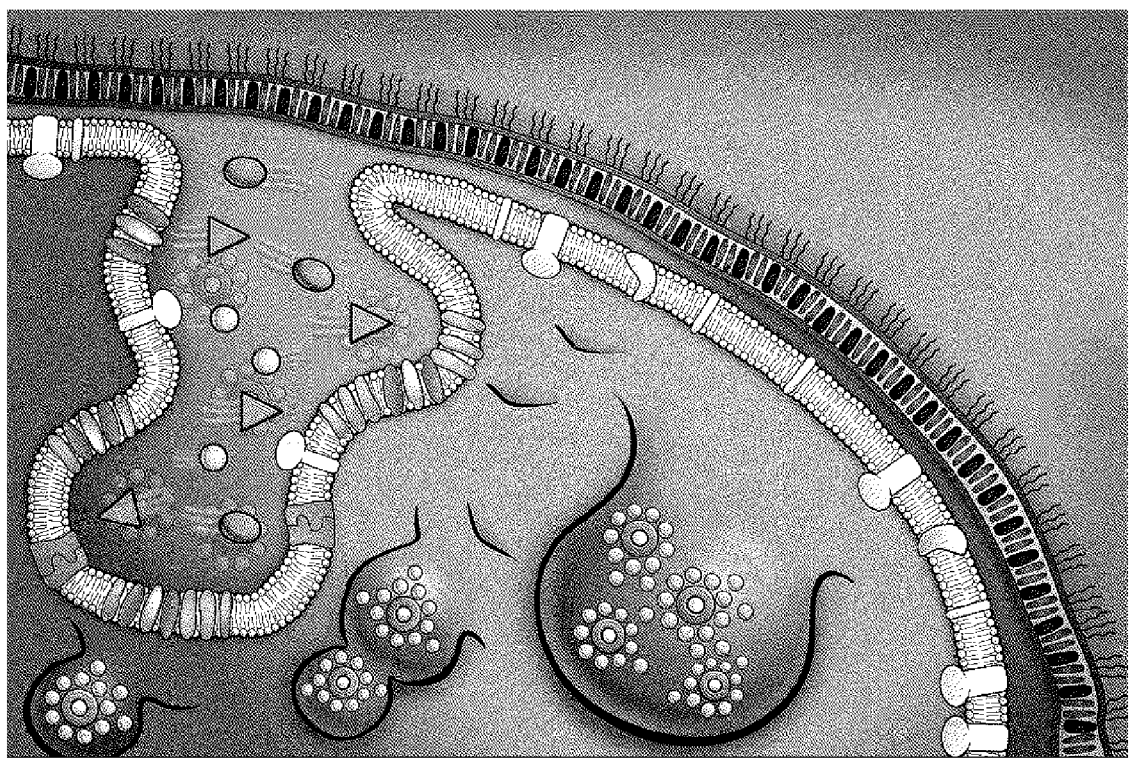
FIG. 3 provides a schematic model of the internalized membrane invaginations of a *Rhodobacter* to compare with the biomimetic characteristics of the invented biomolecule sequestration liquor, in accordance with features of the present invention.

Protein Preparation
Details:

RCs were prepared from *Rhodobacter* (*R.*) *sphaeroides* or *R. capsulatus* expression strains using semi-automated methods as previously described in C. Kirmaier et al., Journal of Physical Chem. B 106, 1799 (2002) and incorporated herein by reference. FIG. 3 is a Model of a Rhodobacter cell underscoring key features of its physiology. Under certain growth conditions, these photosynthetic bacteria produce large quantities of a new intracytoplasmic membrane (ICM) to house the coordinately-induced proteins. The proteins used in this study are abundantly expressed and readily isolated from this organism. The lamellar phase of the complex fluid closely depicts the natural environment of the ICM.

In short, cells were cultured in rich YCC medium and harvested by pelleting at 12,500×g for 7 minutes at 4° C. in an Avanti Centrifuge J-20 XP (Beckman-Coulter). Pellets were resuspended in 10mM Tris pH 7.8, 10mM NaCl buffer and centrifuged at 12,500×g for 7 minutes at 4° C. Pellets were resuspended in fresh 10mM Tris pH 7.8, 10mM NaCl buffer and lysed by sonication and three serial runs through a model M-110L Microfluidizer Processor (Microfluidics). The resulting solution was centrifuged at 22,000×g for 15 minutes at 4° C. and then the membranes (supernatant) were ultracentrifuged at 245,000×g for 120 minutes at 4° C. The supernatant was discarded and membrane pellets were resuspended in 12.5 ml 10mM Tris pH 7.8, 10mM NaCl buffer per gram. RCs were solubilized from the intracytoplasmic membranes by incubation in 1% LDAO (v/v; Fluka) at 37° C. while stirring in the dark for 2-3 minutes at 37° C. for *R. sphaeroides* and 30° C. for *R. capculatus*.

Disrupted membrane suspensions were then ultracentrifuged at 245,000×g for 120 minutes at 4° C. Solubilized membrane proteins (found in the supernatant) were then filtered (0.45 µm) and purified using customized, automated scripts on an ÄKTA™-FPLC™. Purification involved affinity chromatography with a 5 mL HiTrap Chelating HP Column (GE Healthcare) prepared with 0.1M $NiSO_4$, using 10 mM Tris pH 7.8, 0.05% LDAO as a wash buffer and 10 mM Tris, 0.05% LDAO, 100 mM imidazole, pH 7.8 as the elution buffer. The sample was then run over a HiPrep™ 26/10 Desalting column (GE Healthcare) and fractionated through automated detection of UV levels.

Desired fractions were combined and concentrated in an Amicon-Ultra 15 30,000 MWCO Centrifuge Filter Device (Millipore). Purified RC samples were concentrated to an $A_{800}$=60 (~20 mg/mL) using UV-Vis-NIR spectrophotometry.

RC samples in detergent micelles were prepared as 20% (v/v) concentrated RCs (*R. sphaeroides* or *R. capsulatus* RCs) in 10 mM Tris pH 7.8, 0.05% LDAO buffer. Samples were transferred into 1-mm-pathlength cuvettes and incubated at 4, 20 or 32° C. Cuvettes, with Teflon stoppers, were additionally sealed with wax and parafilm to prevent sample evaporation.

Complex Fluid
Formulation Detail:

Complex fluids were prepared as previously described in P.D. Laible et al., J Physical Chem. B, 109, 23679-23686 (2005) and incorporated by reference. In brief, a saturated phospholipid (e.g., 1,2-Dimyristoyl-sn-Glycero-3-Phosphocholine, DMPC), a polymer (often introduced as a lipopolymer, 1,2-Dimyristoyl-sn-Glycero-3-Phosphoethanolamine-N-[Methoxy(Polyethylene glycol)-2000], DMPE) and a co-surfactant (e.g., N,N-dimethyldodecylamine-N-oxide, LDAO) were dispersed in water at 4° C. For example, to make 1g of proteo-complex fluids (prior to RC introduction), 0.823 weight fraction water (546.37µL), 0.023 weight fraction LDAO (76.63µL 30% LDAO in $H_2O$), and 0.154 weight fraction lipid—such that the polymer-to-phospholipid ratio was held at 8 mol %—(0.1145g DMPC, M.W. =677.94; 0.0395g DMPE, M.W. =2693.32) were combined. The components spontaneously self-assembled into a noncovalent, uniform, and optically transparent aggregate, upon repeated thermal cycling between 4° C. and 50° C.

Proteo-Complex Fluid
Detail Samples:

Proteo-complex fluids were prepared as previously described in Laible et al, and incorporated herein by reference. In brief, 20% (v/v) concentrated RCs (*R. sphaeroides* or *R. capsulatus* RCs—as described above) were introduced into the complex fluid (created above) following incubation of both components at 4° C. (i.e., a low viscosity or "micellar" state of the complex fluids). Generally, the protein is mixed with the complex fluid and temperature cycled between low (often micellar) and high viscosity (often solid lamellar) states. Suitable mixing temperatures are less than 37° C. Typical temperatures are from 0 to 10° C.

The number of cycles can vary empirically, but a suitable number of cycles is that which will cause homogenous dispersion of the protein throughout the complex fluid, so that no concentration gradients of any component exists. The composition of the complex fluid is produced in a manner that corrected for the additional water and LDAO introduced by the RC samples in detergent buffer at this step. For example, to make 1 g of proteo-complex fluids, 200 µL of RCs (created above; suspended in 10 mM Tris pH 7.8, 0.05% LDAO detergent buffer) were added to the complex fluid preformulation (created above). This resulted in 0.823 weight fraction water, 0.023 weight fraction LDAO, 0.154 weight fraction lipid (DMPC, DMPE), with a 20% (v/v) RC concentration in the final proteo-complex fluid samples. (Upscaling was achieved using these described mass and volume ratios). Mixing was accomplished by pipetting and thermal cycling between 3° C. and 25° C. Samples were then aliquoted into 1-mm-pathlength cuvettes which were sealed with a stopper, wax and parafilm and incubated at 4, 20 or 32° C.

Stability Detail of Proteins Inserted in Invented Proteocomplex Fluid

Three distinct, temperature-induced phases of the complex fluids were assessed on their ability to sustain RC complexes in native (i.e. active) configurations and where compared to control RC samples maintained in detergent buffer at similar temperatures. Our results show that RCs maintain a higher degree of stability in complex fluids at all phases and temperatures tested relative to RCs suspended in detergent micelles; enhancements are most dramatic with materials stored in the lamellar, gel phase (a high viscosity state). Viscosity states range from liquid through solid phases, whereas the gel phase applies here.

Figure 4:
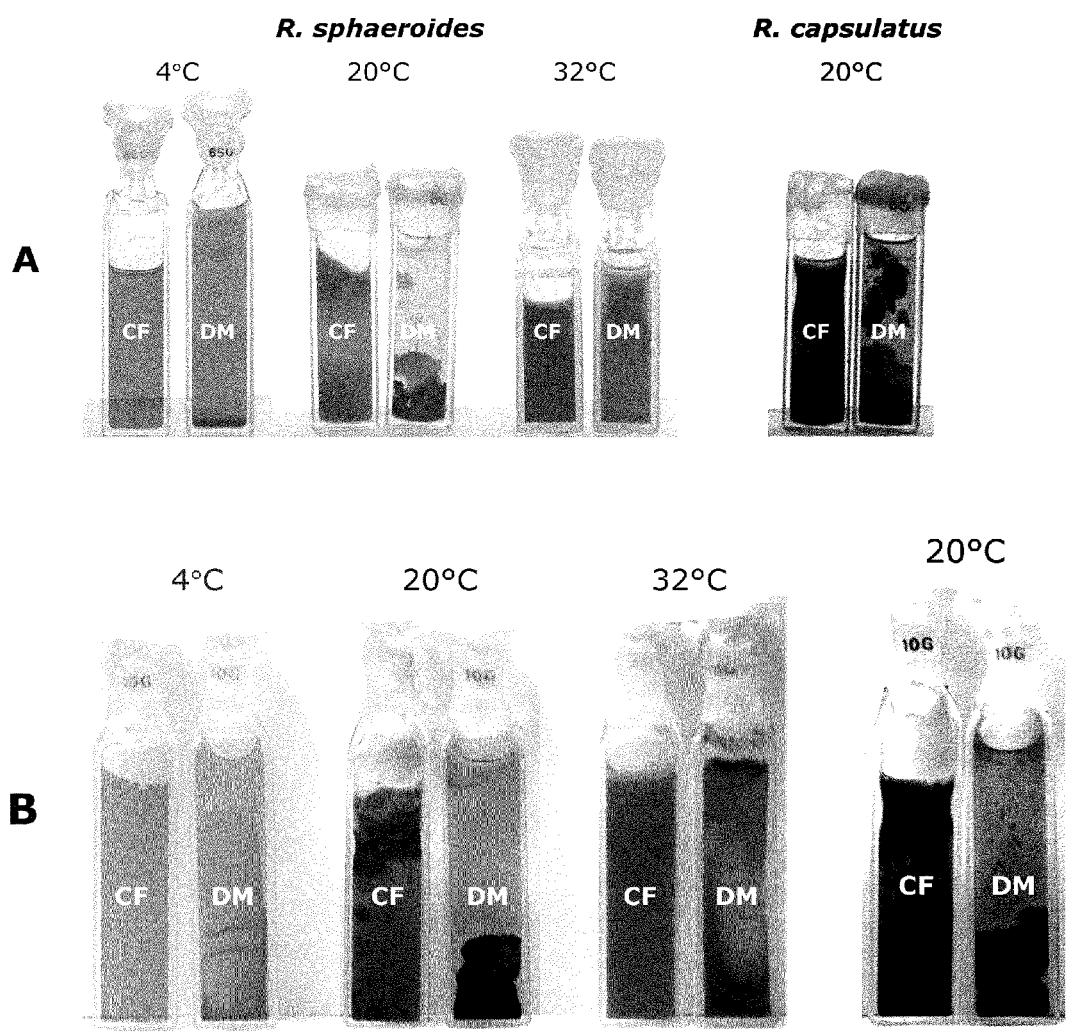
FIG. 4 are photographs comparing samples of proteins stored in detergent micelles, versus those stored via the instant method; in accordance with features of the present invention.
Figure 7:
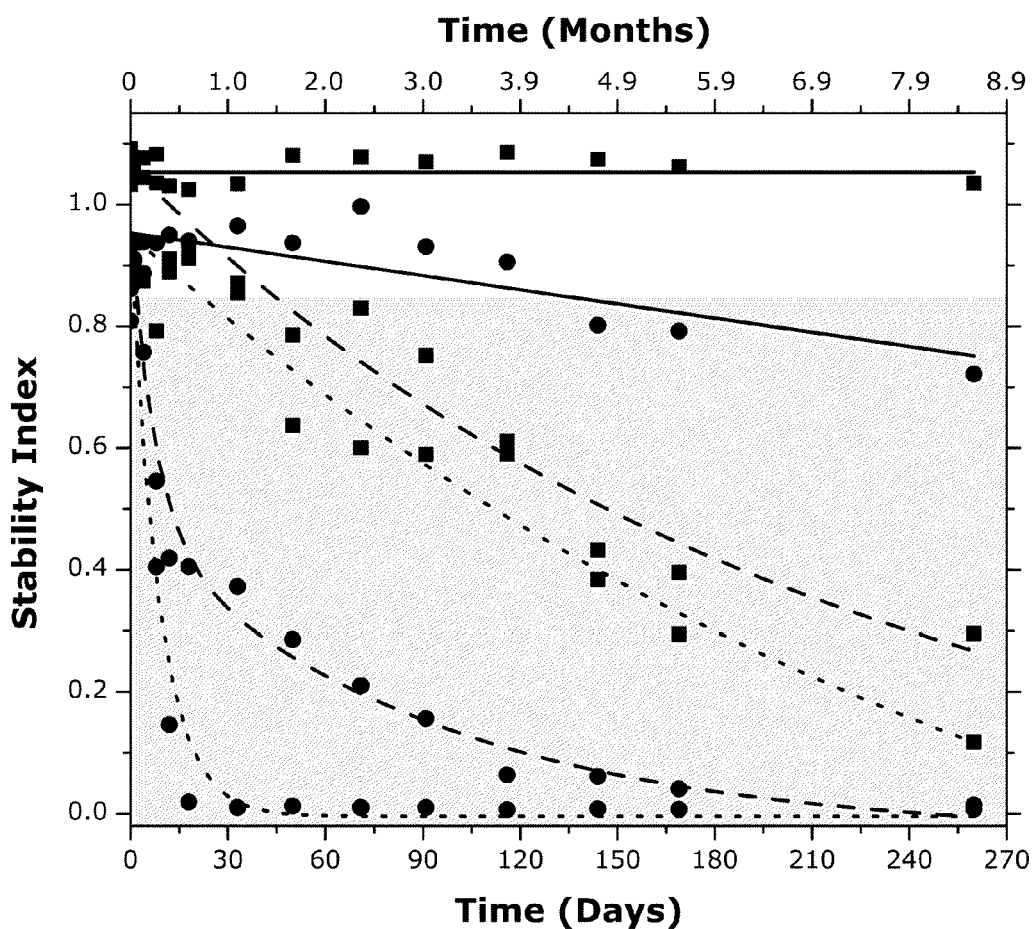
FIG. 7 is UV-Vis-NIR spectra comparing protein integrity, at various temperatures and stored using typical vehicles, versus protein stored via the instant protocol, in accordance with features of the present invention.
Figure 8B:
Figure 8B:
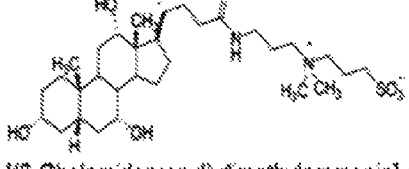
Figure 8B:
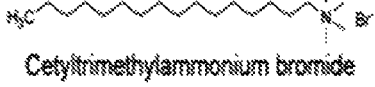
Figure 8B:
Figure 8B:
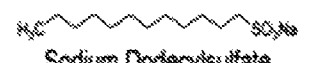
Figure 8B:
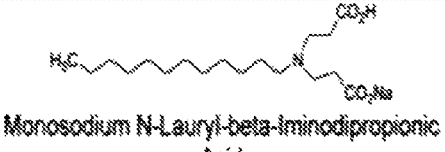
Figure 8C:
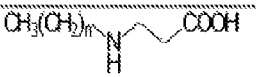
Figure 8C:
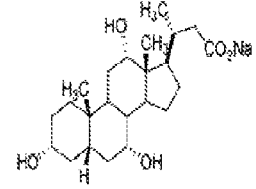
Figure 8C:
Figure 8C:
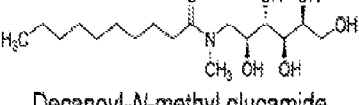
Figure 8C:
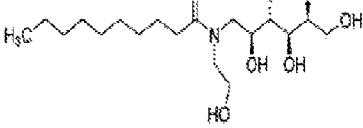
Figure 8C:
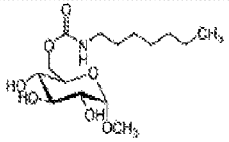

UV-Vis-NIR spectroscopic results show that the longevity of samples in the complex fluid was increased by up to an order of magnitude (from days to months, depending upon the temperature) compared with membrane proteins and protein complexes suspended in detergent micelles (FIG. 7). This increase was most pronounced in samples incubated at temperatures above the phase transition of the fluid. Differences in relative stability extended to visually-discernable traits (e.g., aggregation and color; FIG. 4). FIG. 4 provides photographs of cuvettes with purified samples of reaction centers from either R. sphaeroides or R. capsulatus at 40 days (A) and 131 days (B). Cuvette samples were incubated at three different temperatures in complex fluids (CF) or an aqueous solution of detergent micelles (DM).

The temperatures surveyed span all phases of the complex fluid: low viscosity (4° C.), transition (20° C.), and gel (32° C.). R. capsulatus samples were studied at 20° C. to further assess the potential of the lamellar phase of the complex fluid. The slight heterogeneity of complex fluid seen at 131 days was not observed until late in the experiment, as seen through its absence at 40 days. The surfactant used for the detergent micelles, N,N-dimethyidodecylamine-N-oxide (LDAO), was also part of the complex fluid formulation. Data shown are representative of two separate experiments.

The stability of purified membrane proteins was markedly improved by incorporation into a polymer/lipid-based complex fluid. The tunability of this material allows for (i) ease of incorporation and recovery of the guest molecules and (ii) use of these samples in a wide range of spectroscopies.

This method utilizes the components of the synthetic biological membrane as disclosed in U.S. Pat. No. 6,537,575, and incorporated herein by reference.

When combined in water, the components possess an inverted phase transition, existing in a liquid-crystalline gel (i.e. highly viscous, solid-like) phase at temperatures above ~20° C. and in a low viscosity (i.e. water-like), micellar state at reduced temperatures (FIG. 1). Thus, the physicochemical and structural properties of this material are tunable. The gel phase mimics a biological membrane and can so be used to stabilize reconstituted integral membrane proteins for long-term storage or for transport between site of purification and site of characterization (FIG. 3). The liquid state at lower temperatures serves as the phase in which membrane proteins can be introduced to the materials, and in which some membrane protein structural assays, mainly those based upon spectroscopy, can be conducted. This protocol optimizes the inventors' observation that proteins are much more stable in the invented proteocomplex fluid at lower temperatures. Proteins are extracted readily from the complex fluid by dilution into a detergent buffer, followed by dialysis at a predetermined temperature. In one embodiment, the temperature is selected from between 0-10° C. and preferably at 4° C.

However, the method is not limited to a defined temperature inasmuch as various method for heating and cooling the loaded storage media (i.e., the utilization of flash freezing techniques are suitable.

Protein Isolation Detail

The bacterial reaction centers from two species of purple bacteria—Rhodobacter sphaeroides and Rhodobacter capsulatus—was studied in buffered detergent micelles (10 mM Tris pH 7.8, 0.05% LDAO) or complex fluid. Proteocomplex fluids were prepared as previously described in U.S. Pat. No. 6,537,575, heretofore incorporated herein by reference.

A saturated phospholipid (e.g., 1,2-Dimyristoyl-sn-Glycero-3-Phosphocholine, DMPC), a polymer (often introduced as a lipopolymer, 1,2-Dimyristoyl-sn-Glycero-3-Phosphoethanolamine-N-[Methoxy(Polyethylene glycol)-2000], DMPE) and a co-surfactant (e.g., N,N-dimethyidodecylamine-N-oxide, LDAO) are dispersed in water at 4° C. The components spontaneously self-assemble into a noncovalent aggregate, upon repeated thermal cycling. In one embodiment, thermal cycling occurs between 4° C. and 50° C. In another embodiment, thermal cycling occurs between micellar and lamellar, gel states. The self-assembled material is both uniform and optically transparent.

Figure 5A:
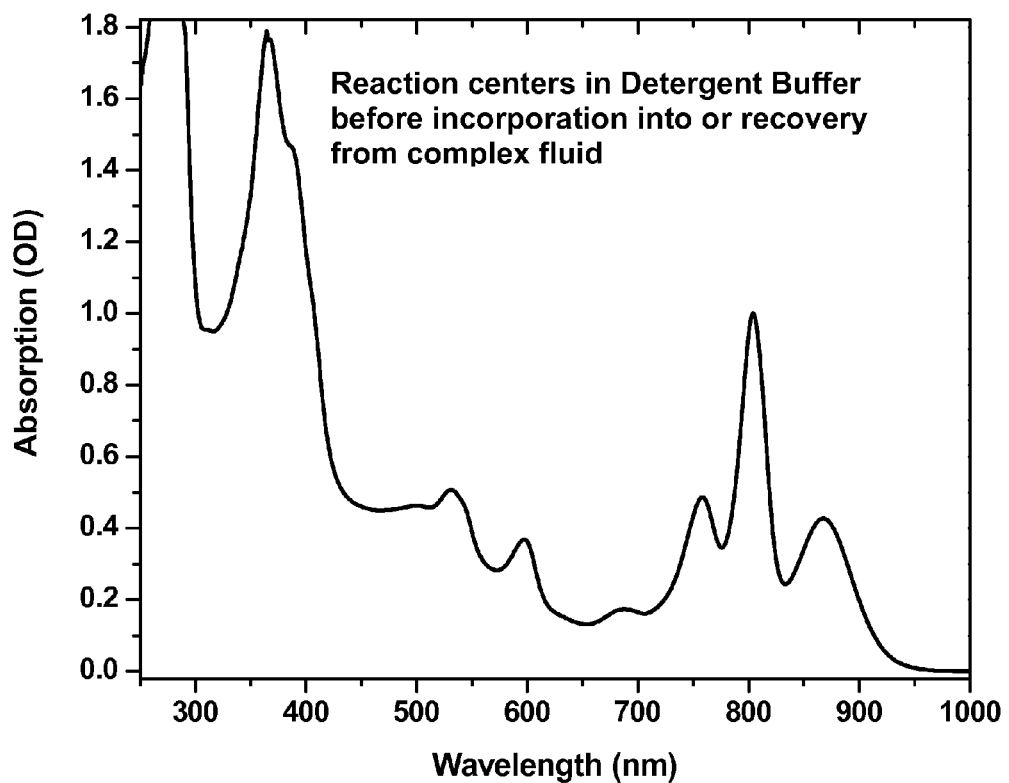
FIGS. 5A-C describes the UV-Vis-NIR spectra of protein stored by typical methods and by the invented method.
Figure 5B:
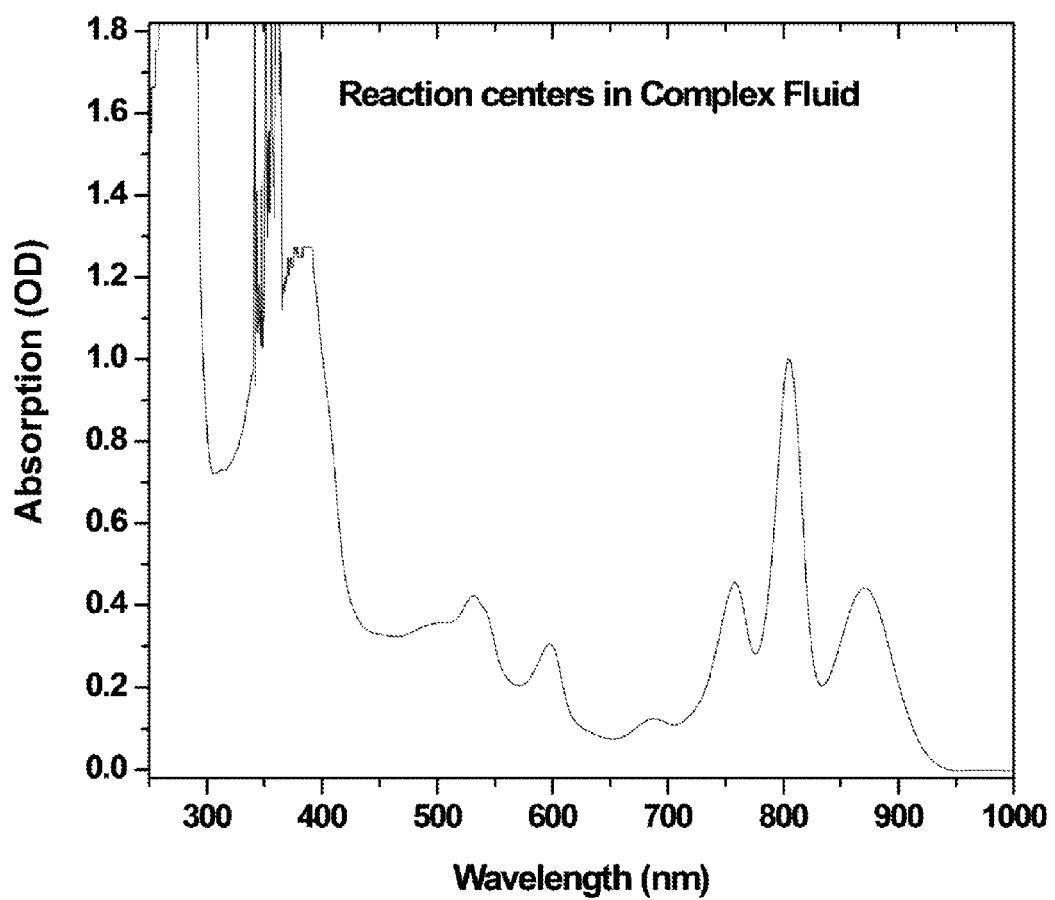
Figure 5C:
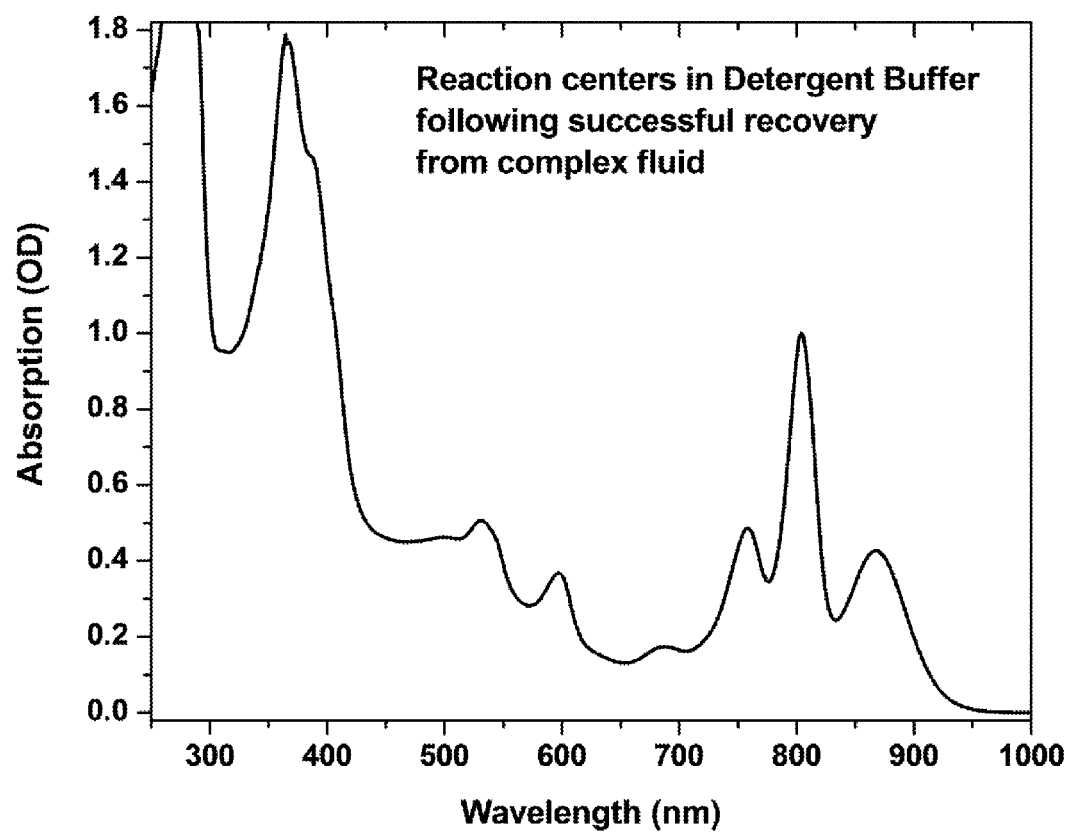
Figure 6A:
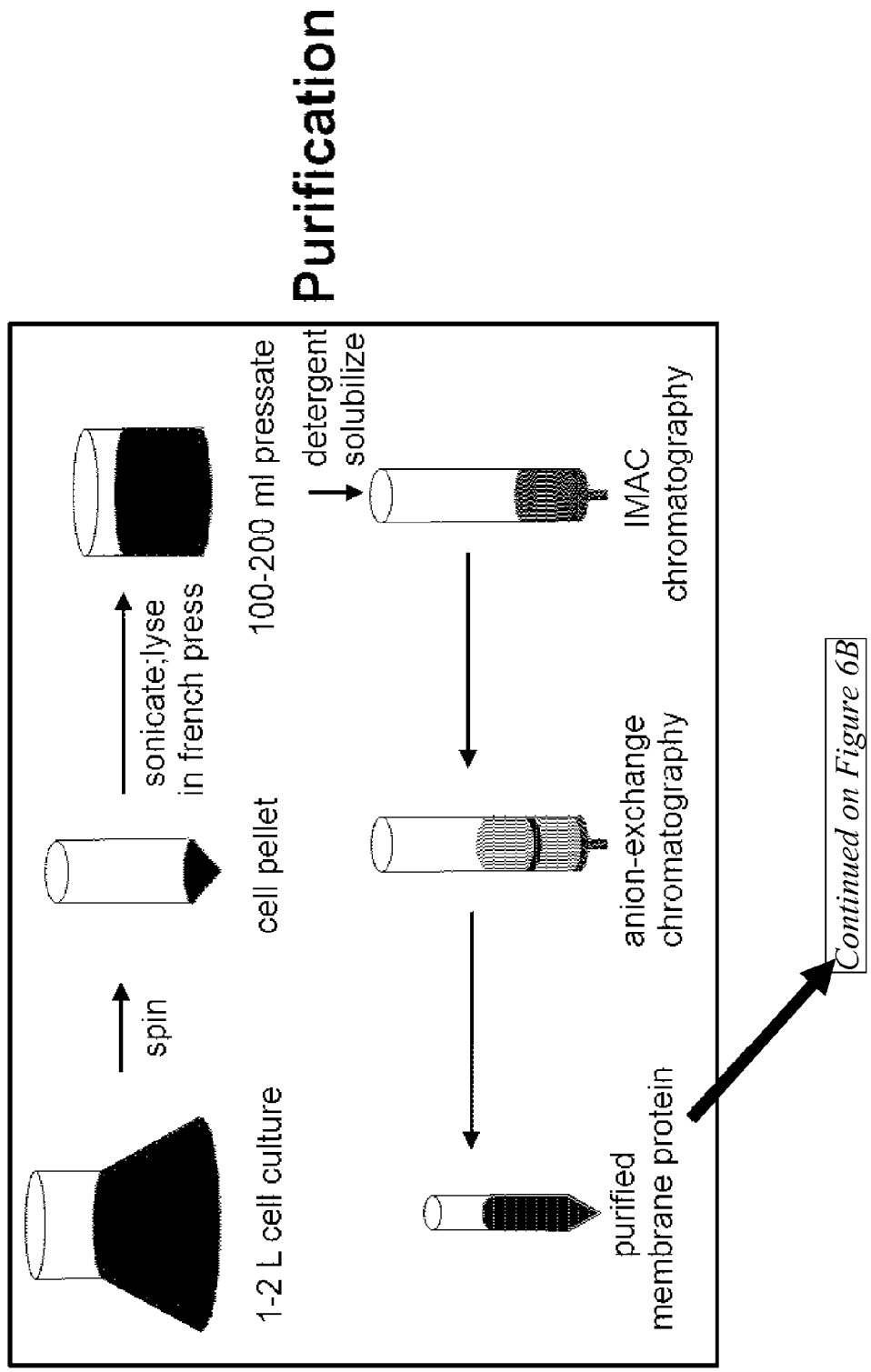
FIGS. 6A-B provide a flowchart as to how protein is extracted via chromatography prior to spectroscopic analysis.
Figure 6B:
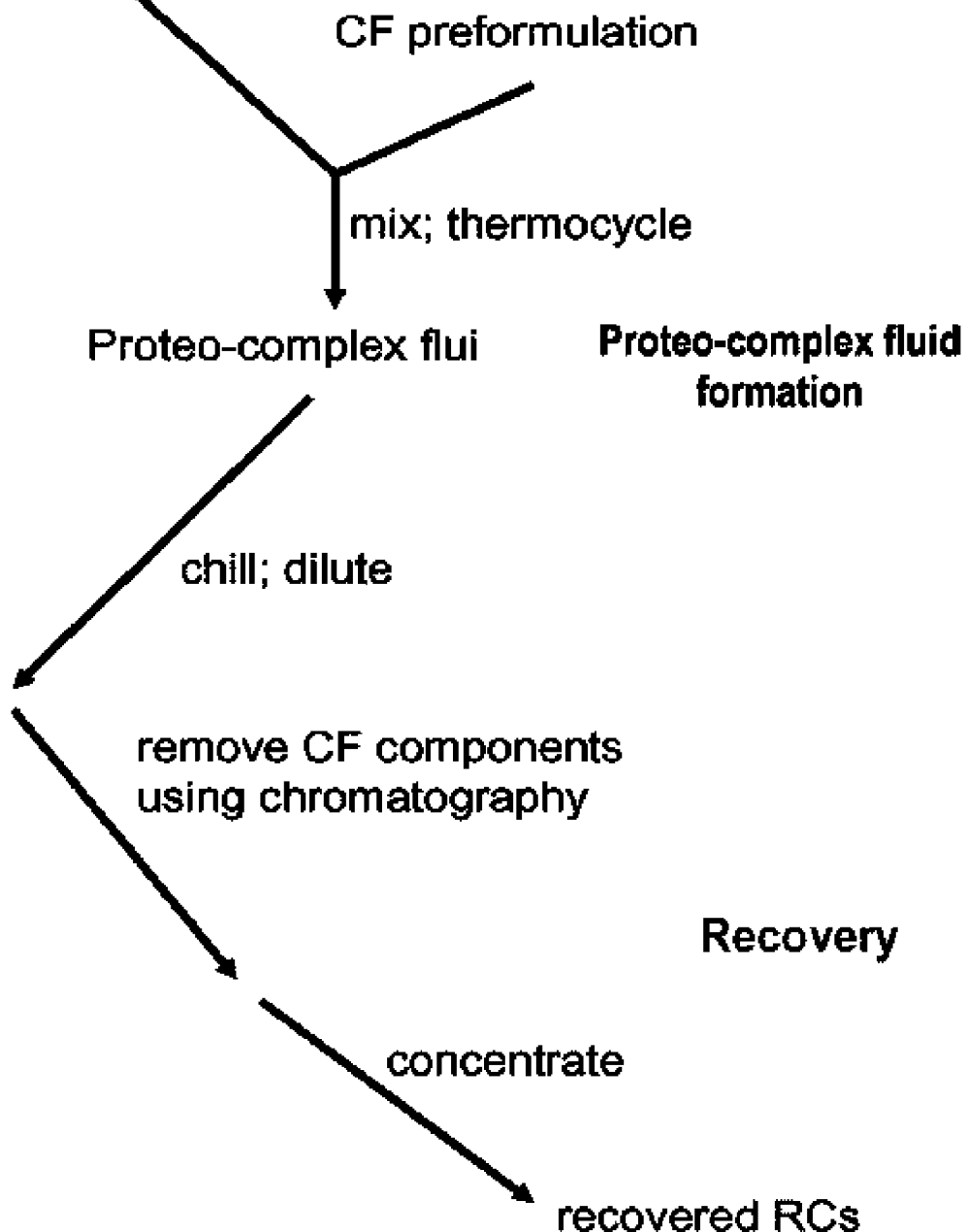

Purified protein is then introduced into the complex fluid following incubation of both components at 4° C. (micellar state of the complex fluids). Mixing was accomplished by pipetting and thermal cycling between 4° C. and 25° C. These experiments exploited the physiology of Rhodobacter sphaeroides and Rhodobacter capsulatus cells regarding the native environment of the host membrane proteins as well as the unique spectral signatures of these proteins in native or denatured states. The room temperature, ground-state absorption spectrum in the near-IR region shows three major absorbance bands, the position and intensities of which are sensitive to the integrity of the co-factors and local protein environment. Samples were incubated in 1-mm-pathlength cuvettes at 4, 20 or 32 degrees Celsius and regularly monitored visually for gross color changes or aggregation (FIG. 4). Sample integrity as a function of time was corrected (FIG. 5) and quantitated through steady-state, UV-Vis-NIR spectroscopy (FIG. 7).

Generally, the invention provides a protocol for the indefinite storage of viable protein in native state.

While the invention has been described with reference to details of the illustrated embodiment, these details are not intended to limit the scope of the invention as defined in the appended claims.

The invention claimed is:

1. A method for the insertion of protein in mixtures and the recovery of the protein from the mixtures, the method comprising:
   a) supplying isolated membrane protein;
   b) mixing the isolated membrane protein with a fluid comprising the saturated phospholipid 1,2-Dimyristoyl-sn-Glycero-3-Phosphocholine, DMPC, the polymer 1,2-Dimyristol-sn-Glycero-3-Phosphoethanolamine N [Methoxy(Polyethylene glycol)-2000] (DMPE), and the co-surfactant N,N-dimethyldodecylamine-N-oxide, LDAO that can exist in a liquid-crystalline gel phase temperatures about 20° C. and above and in a liquid at lower temperatures, so as to form a mixture;
   c) cycling the mixture between a first temperature and a second temperature;

d) diluting the mixture in detergent buffer so as to lower its viscosity; and e) separating the protein from the fluid.

2. The method as recited in claim 1 wherein the protein and fluid is mixed at a temperature whereat the fluid is a liquid.

3. The method as recited in claim 1 wherein the protein and fluid is mixed at temperatures less than 37 C.

4. The method as recited in claim 1 wherein the first temperature is selected as a temperature whereat the fluid is a liquid.

5. The method as recited in claim 1 wherein the second temperature is selected as a temperature whereat the fluid is a gel.

6. The method as recited in claim 1 wherein the protein is mixed with the fluid in a low viscosity micellar state.

7. The method as recited in claim 1 where storage is in micellar state.

8. The method as recited in claim 1 wherein the protein is stored in the fluid in the solid, lamellar state.

9. The method as recited in claim 1 where recovery of intact protein is achieved by dilution and separation.

10. The method as recited in claim 9 where dilution is facilitated by complex fluid in micellar state.

11. The method as recited in claim 1 where the protein is stabilized within the fluid.

12. The method as recited in claim 11 where both the protein and the fluid are soluble.

13. The method as recited in claim 12 where the protein and the fluid are both membrane bound.

14. The method as recited in claim 12 where the protein and the fluid are soluble and membrane bound.

15. The method as recited in claim 8 where the protein is sequestered in either within lipids or outside lipids.

16. The method as recited in claim 1 wherein the fluid comprises dimyristoylphosphatidylcholine, dimyristoyl phosphatidylethanolamine, and lauryldimethlamine-oxide.

17. The method as recited in claim 9 wherein the protein is separated from the complex fluid by dilution into a detergent buffer, followed by dialysis at a predetermined temperature.

18. The method as recited in claim 17 wherein the predetermined temperature is selected from between 0 and 10° C.

19. The method as recited in claim 1 wherein the protein is ordered within the fluid via electrophoresis or isoelectric fusion or magnetic field induction.

* * * * *